United States Patent [19]

Inoue

[11] Patent Number: 5,388,319
[45] Date of Patent: Feb. 14, 1995

[54] METHOD FOR MAKING ORGANISM DEPOSIT-INHIBITING PIPE

[75] Inventor: Shunji Inoue, Nagoya, Japan

[73] Assignee: NGK Insulators, Ltd., Japan

[21] Appl. No.: 27,780

[22] Filed: Mar. 8, 1993

[30] Foreign Application Priority Data

Mar. 24, 1992 [JP]  Japan .................. 4-066269
Apr. 14, 1992 [JP]  Japan .................. 4-094298

[51] Int. Cl.⁶ ............................................. B21K 29/00
[52] U.S. Cl. ............................. 29/416; 29/890.141; 29/890.144; 29/435; 138/154; 148/411; 148/519
[58] Field of Search ............. 29/416, 463, 435, 890.1, 29/890.14, 890.144, 890.141, 432; 138/147, 154, 173; 148/411, 285, 519; 114/222; 204/147, 148, 197

[56] References Cited

U.S. PATENT DOCUMENTS

| | | | |
|---|---|---|---|
| 1,547,609 | 7/1925 | Robinson et al. | 29/435 |
| 1,699,911 | 1/1929 | Palmer | 29/890.144 |
| 1,964,289 | 6/1934 | Harrah | 29/890.144 |
| 2,139,497 | 12/1938 | Hensel et al. | 420/490 |
| 2,422,477 | 6/1947 | Driver | 148/536 |
| 3,103,103 | 9/1963 | Liddell | 24/19 |
| 3,137,642 | 6/1964 | Johns | 204/148 |
| 3,260,661 | 7/1966 | Kemp et al. | 204/148 |
| 3,455,808 | 7/1969 | Raclot | 204/148 |
| 3,620,943 | 11/1971 | White | 204/148 |
| 3,848,308 | 11/1974 | Kaval | 29/416 |
| 4,202,858 | 5/1980 | Bruce et al. | 422/243.6 |
| 4,257,459 | 3/1981 | Jenks | 138/147 |
| 4,334,345 | 6/1982 | Jenks | 29/890.14 |
| 4,496,444 | 1/1985 | Bagnulo | 204/197 |
| 4,551,187 | 11/1985 | Church et al. | 148/411 |
| 5,210,947 | 5/1993 | Donnelly | 29/890.144 |

FOREIGN PATENT DOCUMENTS

0510850  10/1992  European Pat. Off. .

OTHER PUBLICATIONS

Database WPI, Week 7834, Derwent Publications Ltd., London, GB; AN 78-61608A & Research Disclosure, vol. RD172118, Aug. 10, 1978, Havant GB.
Database WPI, Week 8537, Derwent Publications Ltd., London, GB; AN 85-225210 & GB-A-2 154 514 (Utd Wire Group PLC) Sep. 11, 1985.

*Primary Examiner*—Timothy V. Eley
*Assistant Examiner*—Khan V. Nguyen
*Attorney, Agent, or Firm*—Parkhurst, Wendel & Rossi

[57] ABSTRACT

The invention provides a method for making an organism deposit-inhibition pipe, which excels in corrosion resistance, dispenses with maintenance work, and offers no toxicity problems. A thin sheet comprising a copper alloy is wound spirally around a round bar and inserted into a resin pipe made up of an electrical insulating material. And the round bar is taken out. The obtained pipe has an inner wall which is covered with the copper thin sheet. The copper alloy has a Be content of 0.2 to 2.8% by weight, and is selected from, e.g., Be—Cu, Be—Co—Cu, Be—Co—Si—Cu and Be—Ni—Cu alloys. The beryllium-copper alloy has a remarkable antifouling effect and provides a continued liberation of copper ions.

11 Claims, 4 Drawing Sheets

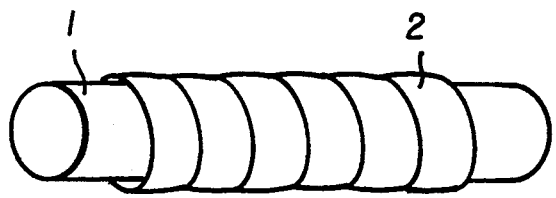
FIG. IA
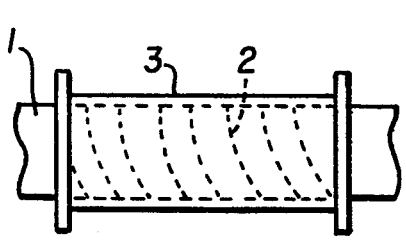
FIG. IB
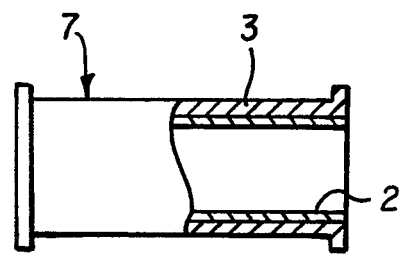
FIG. IC
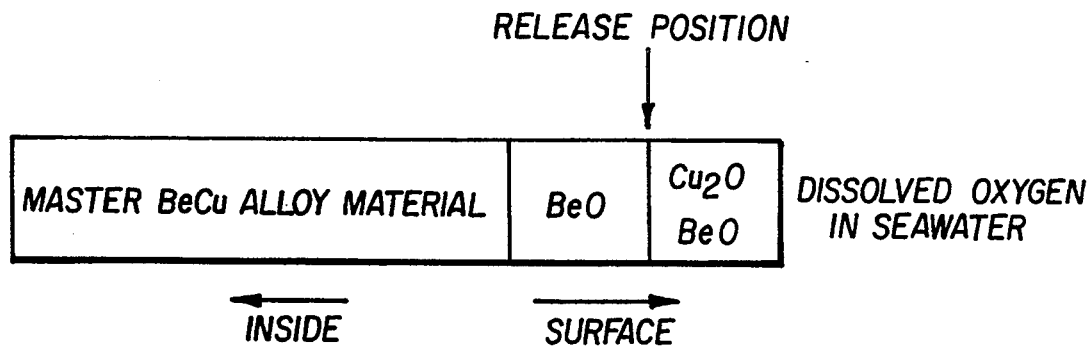
FIG. 2
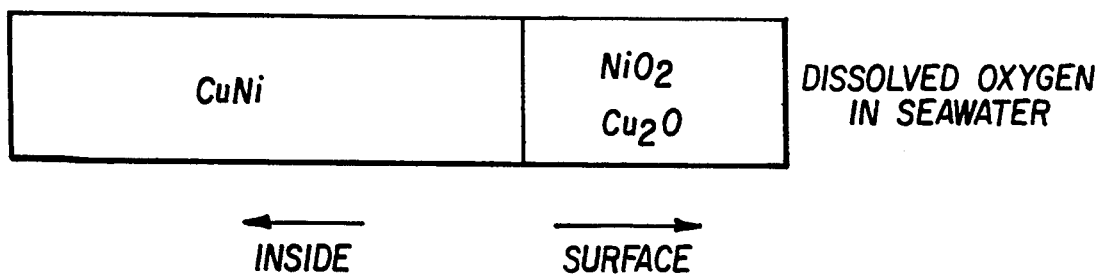
FIG. 3

METHOD FOR MAKING ORGANISM DEPOSIT-INHIBITING PIPE

BACKGROUND OF THE INVENTION

The present invention relates to an antifouling structure and method effective to inhibit deposition of oceanic organisms such as barnacles, blue mussels, and seaweed, hereinafter referred to as an organism deposit-inhibition structure.

Offshore or marine structures in contact with seawater are always exposed to contamination by oceanic organisms, resulting in damage to appearance or malfunction. For instance, ships suffer a driving force drop when many forms of oceanic organisms are deposited onto their bottoms, etc., and thermoelectric power plants are forced to stop operation when various forms of oceanic organisms are built up on their seawater intake pits, because a serious problem arises in connection with the circulation of a seawater serving as a cooling medium.

Among scores of techniques for inhibiting marine deposits studied so far in the art, there is typically now available a method for protecting an offshore structure against contamination, in which the surface of that structure in contact with seawater is coated with a coating material containing cuprous oxide or organotin.

Another method is disclosed in JP-A-60-209505 that is directed to an adhesive member for inhibiting oceanic deposits, which comprises a sheet of copper or a copper alloy, a primer layer provided on one surface thereof, and an adhesive material layer formed on the primer layer.

A grave problem with the method using a coating material, however, is that the coating material has a service life of as short as one year, since even when applied in a thick layer, it is likely to peel away. Accordingly, there is needed troublesome maintenance work in which the coating material must be renewed each year.

The oceanic organism deposit-inhibiting member disclosed in JP-A-60-209505, on the other hand, is found to be less than satisfactory in terms of corrosion resistance and antifouling effect, because of the use of a copper or a copper-nickel (Cu—Ni) alloy.

Our years of study have now revealed that the application of a beryllium-copper alloy to an offshore structure achieves a much-more excellent antifouling effect. The reason would be that beryllium and copper ions interact synergistically, producing a great effect on inhibiting oceanic organisms from having access to the offshore structure and preventing their propagation. In other words, we have now found that the beryllium-copper alloy has a combined effect both on inhibiting marine deposits and on the continued liberation of copper ions.

A main object of the invention is to provide a method for making an organism deposit-inhibiting pipe, which can be easily produced, excels in the capability to inhibit deposition of organisms and durability, dispenses with maintenance work, and offers no toxicity problem.

SUMMARY OF THE INVENTION

According to one aspect of the invention, there is provided a method for making an organism deposit-inhibiting pipe, characterized in that a thin sheet made up of a copper alloy is wound spirally around a round bar, an electrical insulating resin layer is formed on an outer surface of the copper alloy thin sheet, and the round bar is taken out.

Preferably, this copper alloy has a beryllium content of 0.2 to 2.8% by weight, and is an alloy selected from the group consisting of Be—Cu, Be—Co—Cu, Be—Co—Si—Cu and Be—Ni—Cu alloys.

According to another aspect of the invention, there is provided a method for making an organism deposit-inhibiting pipe, characterized in that a thin strap made up of a copper alloy is wound spirally, a convex portion and a concave portion of the copper alloy thin strap, which are adjacent to each other, are engaged to prevent the copper alloy thin strap from moving in the axial direction, and an electrical insulating resin layer is formed on an outer surface of the copper alloy thin strap.

According to a further aspect of the invention, there is provided a method for making an organism deposit-inhibiting pipe, characterized in that a thin sheet made up of a copper alloy is wound spirally to make an inner pipe, a first electrical insulating resin layer is formed on an outer surface of the inner pipe, the obtained pipe is cut into a plurality of members, end faces of the cut members are faced and connected to each other, and a second resin layer is formed on an outer surface of the connected members.

According to a still further aspect of the invention, there is provided a method for making an organism deposit-inhibiting pipe, characterized in that a thin sheet made up of a copper alloy is wound spirally around a round bar, a first insulating resin layer is formed on an outer surface of the copper alloy thin sheet, the round bar is taken out, the obtained pipe is cut along inclined cutting plane lines into a plurality of members, end faces of the cut members are faced and connected, and a second resin layer is formed on an outer surface of the connected members.

According to a further aspect of the invention, there is provided a method for making an organism deposit-inhibiting pipe, characterized in that a thin strap made up of a copper alloy is wound spirally, a convex portion and a concave portion of the copper alloy thin strap, which are adjacent to each other, are engaged to prevent the copper alloy thin strap from moving in the axial direction, a first electrical insulating resin layer is formed on an outer surface of the copper alloy thin strap, the obtained pipe is cut into a plurality of members, end faces of the cut members are faced and connected, and a second resin layer is formed on an outer surface of the connected members.

Preferably, this copper alloy has a beryllium content of 0.2 to 2.8% by weight, and is an alloy selected from the group consisting of Be—Cu, Be—Co—Cu, Be—Co—Si—Cu and Be—Ni—Cu alloys.

BRIEF DESCRIPTION OF THE DRAWINGS

The invention will now be explained, more specifically but not exclusively, with reference to the accompanying drawings, in which:

FIGS. 1(A)–1(C) are illustrations of how an organism deposit-inhibiting pipe is made according to the first embodiment of the first aspect of the invention, FIG. 2 is a schematic representation of what state an oxide film of the beryllium-copper alloy according to the invention is in, FIG. 3 is a schematic representation of what state an oxide film of a cupronickel, provided for comparative purposes, is in.

DESCRIPTION OF THE PREFERRED EMBODIMENTS

Figure 4:
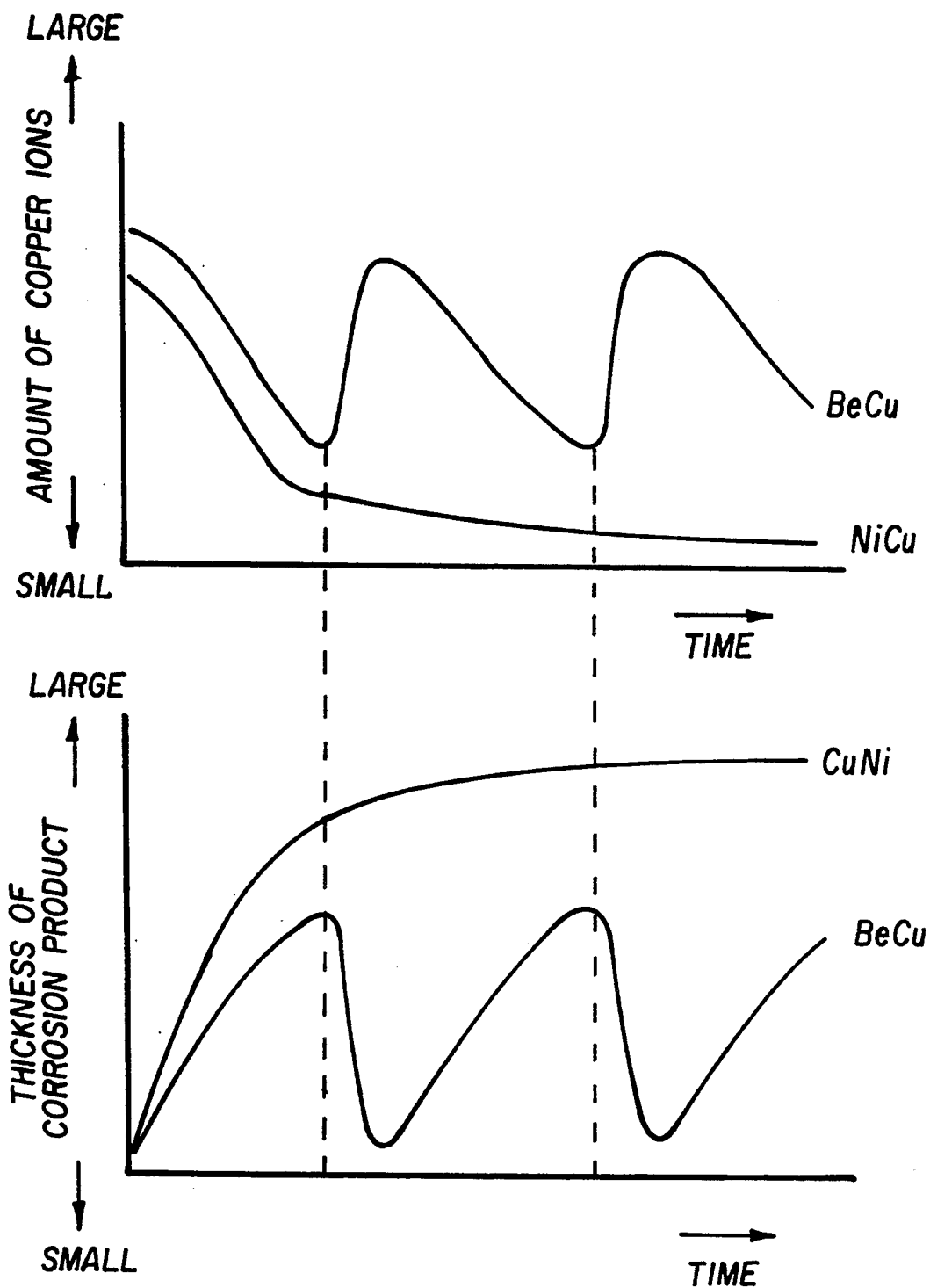
FIG. 4 is a schematic illustration wherein beryllium copper is compared with cupronickel in terms of changes-with-time in the amount of copper ions liberated and the thickness of corrosion product.

The copper alloy used in the invention has a beryllium content ranging from 0.2% by weight to 2.8% by weight, and may be selected from the group consisting of Be—Cu, Be—Co—Cu, Be—Co—Si—Cu and Be—Ni—Cu alloys.

Typical compositions of the copper alloy used in the invention are:

(1) 0.2 to 1.0% by weight of beryllium, 2.4 to 2.7% by weight of cobalt and the balance being copper and inevitable impurities, (2) 0.2 to 1.0% by weight of beryllium, 1.4 to 2.2% by weight of nickel and the balance being copper and inevitable impurities, (3) 1.0 to 2.0% by weight of beryllium, 0.2 to 0.6% by weight of cobalt and the balance being copper and inevitable impurities, and (4) 1.6 to 2.8% by weight of beryllium, 0.4 to 1.0% by weight of cobalt, 0.2 to 0.35% by weight of silicon and the balance being copper and inevitable impurities.

Preferably, the contents of beryllium (Be), cobalt (Co), nickel (Ni) and silicon (Si) selectively incorporated in the copper alloy lie in the respective ranges:

Beryllium - 0.2 to 2.8% by weight
Cobalt - 0.2 to 2.7% by weight
Nickel - 1.4 to 2.2% by weight
Silicon - 0.2 to 0.35% by weight Set out below are for what purpose the above elements are added and why the upper and lower limits thereof are set at the above values.

Beryllium: 0.2–2.8% by Weight

Beryllium is used to (1) protect the structure, when immersed in seawater, against contamination by liberating beryllium ions, (2) improve the strength and properties, e.g., corrosion resistance, of the copper alloy, (3) enhance the productivity of the copper alloy as by heat treatment and grain size regulation, and (4) improve the processability and castability of the copper alloy. At below 0.2% by weight the above-described effects (1)–(4) are unachievable. At higher than 2.8% by weight, not only is there some metalleability drop but a cost-effective problem arises as well.

Cobalt: 0.2 to 2.7% by Weight

Cobalt is used to form a fine CoBe compound and disperse it throughout the alloy matrix, thereby improving the mechanical properties and productivity of the copper alloy. At less than 0.2% by weight this effect is not easily achieved. At higher than 2.7% by weight, not only is there some material flowability drop but there is little or no improvement in the above-described effect as well. In addition, a cost-effective problem arises.

Nickel: 1.4–2.2% by Weight

Nickel is used to form a fine NiBe compound and disperse it throughout the alloy matrix, thereby improving the mechanical properties and productivity of the copper alloy. At less than 1.4% by weight this effect is not easily achieved. At higher than 2.2% by weight, not only is there some material flowability drop but there is little or no improvement in the above-described effect as well. In addition, a cost-effective problem arises.

Silicon: 0.2–0.35% by Weight

Silicon is used to improve the material flowability of the copper alloy. At less than 0.2% by weight this effect is not easily achieved. At higher than 0.35% by weight the resulting alloy becomes brittle with a toughness drop.

As a result of our years of experimentation and research, it has turned out that the beryllium-copper alloy has a combined effect both on preventing contamination and on the continued liberation of copper ions. Detailed explanation will now be made to the antifouling effect and the continued action on liberating copper ions.

(1) Antifouling Effect

As well known from literature, the order of ionization tendency among beryllium, copper and nickel is expressed by

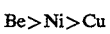

Be>Ni>Cu

In other words, beryllium ions are more likely to be liberated than nickel ions, and nickel ions are more likely to be liberated than copper ions. In the case of a beryllium-copper combination, beryllium is first ionized to form a local cell, which has an effect on preventing deposition of oceanic life contaminants due to its current effect, while beryllium ions take on the form of internal oxidation. By this internal oxidation, a BeO film is first formed, as typically shown in FIG. 2. This BeO film, because of being porous, allows copper ions to be liberated, forming $Cu_2O + BeO$ on the surface. This liberation of copper ions into seawater produces an antifouling effect.

(2) Continued Action on Liberating Copper Ions

The above-mentioned effect (1) on preventing contamination makes another contribution to providing a continued liberation of copper ions, that is, the beryllium-copper combination enables the antifouling function to be maintained ceaselessly. While in contact with seawater, the beryllium-copper combination forms on its surface an intimate surface oxide ($Cu_2O$), just below which a porous oxide film of BeO is formed, as can be seen from FIG. 2. Thus, the liberation of copper ions into seawater is maintained, while this film increases in volume by the oxidation. When the volume increase reaches a certain level, the surface oxide film peels away from the porous oxide or BeO layer. This would enable electrochemical action and the liberation of copper ions to be maintained over an extended period of time.

The continued action of the beryllium copper on the liberation of copper ions will now be explained with reference to FIG. 4 that is a graphic representation showing the results of comparison of beryllium copper with cupronickel.

When the corrosion (oxidation) product reaches a certain thickness, it peels away from the beryllium copper (BeCu), as can be best seen from FIG. 4. Then, the beryllium-copper alloy is again exposed on the surface to seawater, and corroded or oxidized for oxide film growth. When this film grows to a certain thickness level, it peels away from the beryllium copper. This process is repeated over and over. The liberation of copper ions, on the other hand, is likely to be reduced with an increase in the thickness of the oxidation product. As the oxidation product peels away, however, the beryllium-copper alloy is again exposed on the surface to seawater, so that there can be an increase in the amount of the copper ions liberated. Thus, the increase and decrease in the amount of the copper ions liberated occur alternately.

The beryllium-copper alloy used in the invention enables copper ions to be continuously liberated by the peeling-off of the oxide film. As a result, the amount of oceanic organisms deposited onto the surface of the beryllium copper is little, if any.

This is in contrast to the comparative cupronickel (CuNi), as can be seen from FIG. 3. With the passing of some years, an intimate nickel oxide ($NiO_2$) or copper oxide ($Cu_2O$) layer is formed on the surface of the cupronickel, reducing the liberation of copper ions, as can be seen from FIG. 4. According to the order of ionization tendency (Be>Ni>Cu), this would be due to the fact the nickel (Ni) is preferentially ionized to form a local cell and so an intimate oxide is formed on the surface of the cupronickel, as can be seen from FIG. 3. As can be seen from FIG. 4, the thickness of the corrosion product on the cupronickel increases with time in an early stage, but its growth rate decreases as time goes by. With this, there is a decrease in the amount of the copper ions liberated. In addition, the corrosion product is less likely to peel away from the cupronickel than from the beryllium copper. Thus, the quantity of the copper ions liberated remains low, making the antifouling effect slender.

It is to be noted that the facts that a beryllium-copper alloy has a remarkable antifouling effect and provides a continued liberation of copper ions have been discovered by us for the first time. Insofar as we are concerned, never until now have such facts been referred to or indicated in literature.

For practical beryllium alloys, various alloys inclusive of JIS 11 ALLOY having a beryllium content of 0.2 to 0.6% by weight and JIS 25 ALLOY having a beryllium content of 1.8 to 2.0% by weight are now available in the art. In view of the antifouling effect, however, a beryllium content of at least 1.6% by weight is preferable. At a beryllium content higher than 2.8% by weight, beryllium does no longer form any further solid solution with copper. In other words, the resulting alloy excels in the antifouling effect but undergoes a gradual decrease in metalleability.

EMBODIMENTS OF THE FIRST ASPECT OF THE INVENTION

Referring now to FIG. 1, there is shown the first embodiment of the first aspect of the invention.

In the first embodiment, a thin sheet 2 made up of a copper alloy, for instance, a beryllium-copper alloy is spirally wound around a round bar 1, as illustrated in FIG. 1(A). A resin layer 3 made up of an electrical insulating material is formed on an outer surface of the beryllium-copper alloy thin sheet 2, as shown in FIG.1(B). Then, the round bar is taken out. The obtained pipe 7 has an inner wall made up of the beryllium-copper alloy thin sheet 2.

This beryllium-copper alloy has a remarkable antifouling effect and provides a continued liberation of copper ions, as already mentioned.

Figure 5:
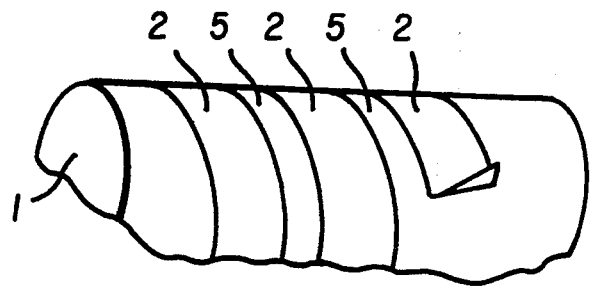
FIG. 5 is an illustration of how a thin sheet made up of a beryllium-copper alloy is wound according to the second embodiment of the first aspect of the invention.

The second embodiment of the first aspect of the invention is illustrated in FIG. 5.

In the second embodiment, a thin sheet 2 made up of a beryllium-copper alloy is spirally wound around a round bar 1 with space 5. The wound beryllium-copper alloy thin sheet 2 is inserted into a pipe 7 made up of resin, as illustrated in FIG. 1(B) and the round bar 1 is taken out. The obtained pipe has an inner wall on which the beryllium-copper alloy thin sheet 2 is partly formed and the resin pipe is exposed in other parts, as shown in FIG. 1(C).

The beryllium-copper alloy of the second embodiment also has a remarkable antifouling effect and its continued effect, thereby preventing deposition and propagation of oceanic organisms.

The third embodiment of the first aspect of the invention will now be explained with reference to FIG. 6.

In this embodiment, a thin sheet 2 made up of a beryllium-copper alloy is spirally wound around a round bar 1 with space 5. Another beryllium-copper alloy thin sheet 2 is wounded to cover the space 5. A resin layer is formed on the beryllium-copper thin sheet 2 and the round bar 1 is taken out. The obtained pipe has an inner wall which is completely covered with the beryllium-copper alloy.

EMBODIMENT OF THE SECOND ASPECT OF THE INVENTION

Figure 7:
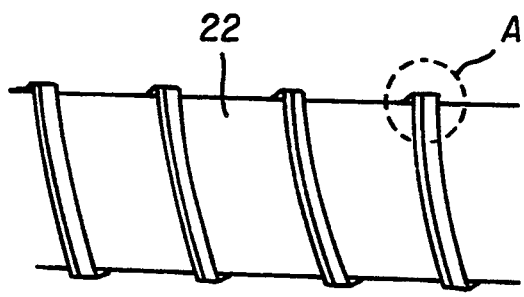
FIG. 7 is an illustration of how an organism deposit-inhibiting pipe is made according to the first embodiment of the second aspect of the invention.
Figure 8:
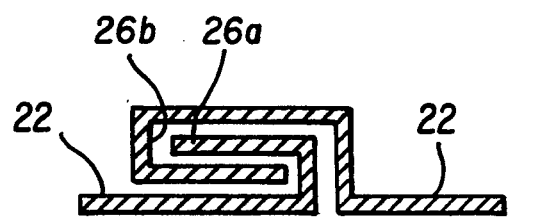
FIG. 8 is an enlarged cut-away, perspective view showing the part marked with A in FIG. 7, and FIGS. 9(A)–9(E) are illustrations of how an organism deposit-inhibiting pipe is made according to the first embodiment of the third aspect of the invention.

The first embodiment of the second aspect of the invention is illustrated in FIGS. 7 and 8.

In this embodiment, a thin strap 22 made up of a beryllium-copper alloy is spirally wound. A convex portion 26a and a concave portion 26b of the beryllium-copper alloy thin strap 22, which are adjacent to each other, are engaged to prevent the beryllium-copper alloy thin strap 22 from moving in the axial direction. Then, an electrical insulating resin layer (not shown) is formed on an outer surface of the beryllium-copper thin strap 22 to make a cylindrical pipe. The obtained pipe has an inner wall which is covered with the beryllium-copper thin strap 22.

EMBODIMENT OF THE THIRD ASPECT OF THE INVENTION

The first embodiment of the third aspect of the invention will now be explained with reference to FIG. 9.

Figure 9A:
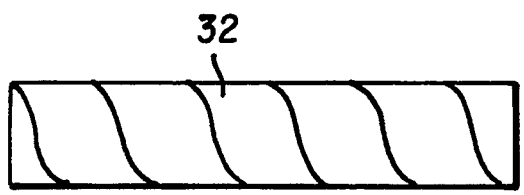
Figure 9B:
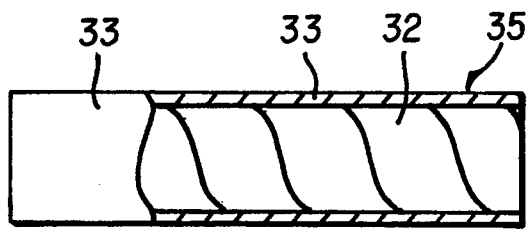
Figure 9C:
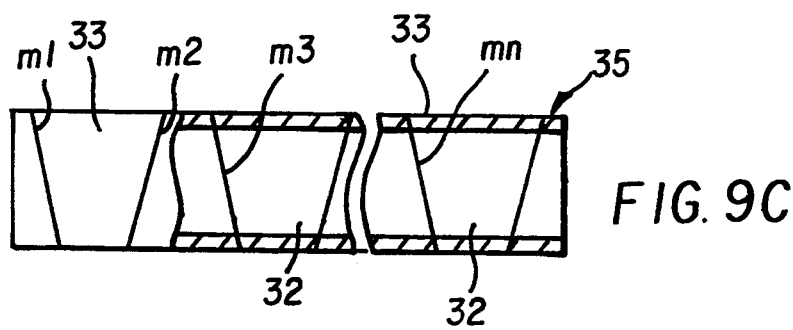
Figure 9D:
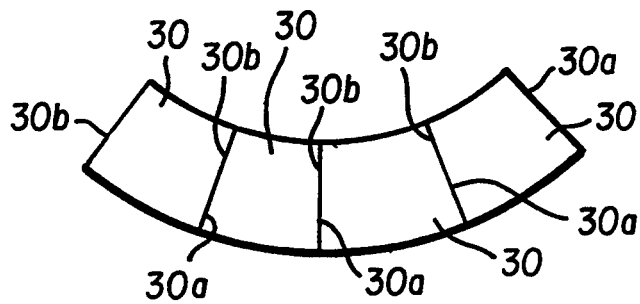
Figure 9E:
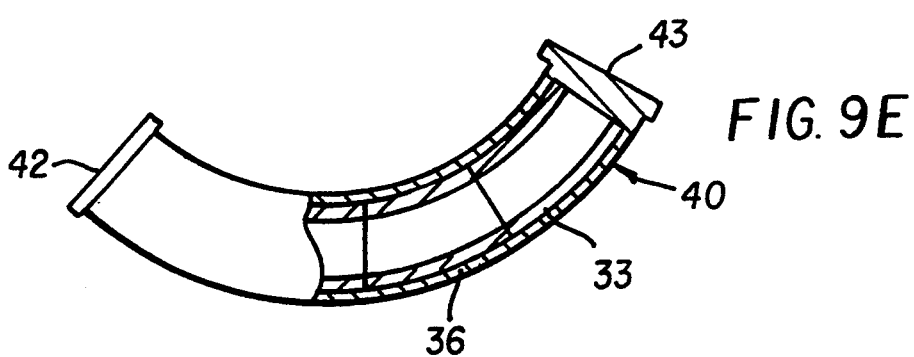

In this embodiment, a thin strap 32 made up of a beryllium-copper alloy is spirally wound to make an inner pipe, as illustrated in FIG. 9(A). An outer casing 33 comprising a first electrical insulating resin layer is formed on an outer surface of the inner pipe to make a cylindrical pipe 35, as shown in FIG. 9(B). Then, the pipe 35 is cut along inclined cutting plane lines m1, m2, m3,-mm to obtain cut members 30 which are of uniform shape and size, as shown in FIG. 9(C). End faces 30a and 30b of the cut members 30 are connected to make a curved pipe, as illustrated in FIG. 9(D). An outer casing 36 comprising a second resin layer is covered on the casing 33, as shown in FIG. 9(E). On the both sides of the obtained curved pipe 40, flanges 42 and 43 are formed.

According to the first embodiment of the third aspect of the invention, the beryllium-copper alloy thin sheet is wound to make the cylindrical pipe, and the outer surface of the cylindrical pipe is covered with the resin layer to make the straight pipe 35. The straight pipe 35 is cut along the predetermined inclined cutting plane lines. The end faces of the cut members 30 are connected to each other. With this method, a curved pipe can be easily produced. In addition, a curvature of a pipe can be easily changed by circumferentially shifting a connecting angle between one end face 30a and another end face 30b of the cut members 30. Therefore, it is possible to make a beryllium-copper alloy pipe with desired curvature.

EMBODIMENTS OF THE FOURTH ASPECT OF THE INVENTION

The first embodiment of the fourth aspect of the invention will now be explained.

In this embodiment, the processes shown in FIG. 1(A), 1(B) and 1(C) are employed in place of the processes shown in FIGS. 9(A) and 9(B). A thin sheet 2 made up of a beryllium-copper alloy is spirally wound around a round bar 1, as illustrated in FIG. 1(A). An electrical insulating resin layer 3 is covered on an outer surface of the beryllium-copper alloy thin sheet 2, as shown in FIG. 1(B). Then, the round bar is taken out. The obtained pipe 7 has an inner wall which is covered with the beryllium-copper alloy thin sheet 2, as illustrated in FIG. 1(C). The processes shown in FIGS. 9(C), (D) and (E) follow this process.

The beryllium-copper alloy of this first embodiment also has a remarkable antifouling effect and its continued effect, thereby preventing deposition and propagation of oceanic organisms.

The second embodiment of the fourth aspect of the invention will now be explained.

In this embodiment, the processes shown in FIG. 5 is employed in place of the process shown in FIG. 9(A). A thin sheet 2 made up of a beryllium-copper alloy is spirally wound around a round bar 1 with space 5. This wound beryllium-copper alloy thin sheet is inserted into a resin pipe, and the round bar is taken out. The obtained pipe has an inner wall on which the beryllium-copper alloy is partly formed and the resin pipe is exposed in other parts. Then, the processes shown in FIGS. 9(C), 9(D) and 9(E) follow this process.

The beryllium-copper alloy of this second embodiment also has a remarkable antifouling effect and its continued effect, thereby preventing deposition and propagation of oceanic organisms.

Figure 6:
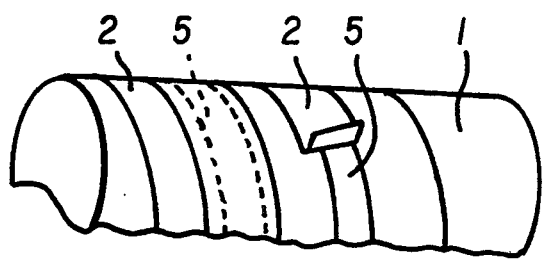
FIG. 6 is an illustration of how a thin sheet made up of a beryllium-copper alloy is wound according to the third embodiment of the first aspect of the invention.

Illustrated in FIG. 6 is the third embodiment of the fourth aspect of the invention.

In this embodiment, the process shown in FIG. 6 is employed in place of the process shown in FIG. 9(A). A thin sheet 2 made up of a beryllium-copper alloy is spirally wound around a round bar 1 with space 5. Another beryllium-copper alloy thin sheet 2 is wound to cover the space 5. A resin layer is formed on the beryllium-copper thin sheet 2 and the round bar 1 is taken out. The obtained pipe has an inner wall which is completely covered with the beryllium-copper alloy. The processes shown in FIGS. 9(C), (D) and (E) follow this process.

EMBODIMENTS OF THE FIFTH ASPECT OF THE INVENTION

The first embodiment of the fifth aspect of the invention will now be explained with reference to FIGS. 7 and 8.

In this embodiment, a thin strap 22 made up of a beryllium-copper alloy is spirally wound. A convex portion 26a and a concave portion 26b of the beryllium-copper alloy thin strap 22, which are adjacent to each other, are engaged to prevent the beryllium-copper alloy thin strap 22 from moving in the axial direction. Then, a first electrical insulating resin layer, which is not shown in the FIGURES, is formed on an outer surface of the beryllium-copper thin strap 22 to make a cylindrical pipe. The obtained pipe has an inner wall which is covered with the beryllium-copper thin strap 22. The processes shown in FIGS. 9(C), 9(D) and 9(E) follow this process.

With the method for making an organism deposit-inhibiting pipe according to the invention, it is possible to make the antifouling pipe for inhibiting deposition of oceanic organisms in relatively simple operation. The antifouling structure provided by this method excels in corrosion resistance, can be maintained in less troublesome operation, presents no toxicity problem, and can effectively inhibit deposition of oceanic organisms.

I claim:

1. A method for making an organism deposit-inhibiting pipe, comprising:
   providing a first thin strip comprised of a beryllium-copper alloy, said first thin strip having opposite first and second edges;
   spirally winding said first thin strip to form an inner layer of a pipe structure; and
   providing a first resin member to cover an outer surface of said first thin strip after the spiral winding step, thereby to provide an outer layer of said pipe structure.

2. The method of claim 1, wherein said beryllium-copper alloy comprises 0.2 to 2.8% by weight beryllium and said beryllium-copper alloy is an alloy selected from the group consisting of Be—Cu, Be—Co—Cu, Be—Co—Si—Cu, and Be—Ni—Cu alloys.

3. The method of claim 1, wherein said first thin strip is wound such that said first and second edges overlap each other.

4. The method of claim 3, wherein said first and second edges comprise convex and concave edge portions, respectively, said first thin strip being spirally wound such that said concave edge portion engages said convex edge portion to prevent separation of the concave and convex edge portions.

5. The method of claim 1, wherein said first thin strip is wound spirally on a cylindrical bar such that said first and second edges are spaced apart from each other.

6. The method of claim 5, wherein said method further comprises a step of spirally winding a second thin strip comprised of a beryllium-copper alloy on said first thin strip to cover said first and second edges of said first thin strip.

7. The method of claim 6, wherein said cylindrical bar is removed after providing said first resin member.

8. The method of claim 1, wherein said first thin strip is spirally wound on a cylindrical bar.

9. The method of claim 8, wherein said cylindrical bar is removed after providing said first resin member.

10. The method of claim 1, wherein said first resin member is electrically insulating.

11. The method of claim 1, further comprising the steps of:

cutting said pipe structure along numerous cutting edges to form numerous cut members wherein said cutting edges extend along an angle with respect to a central axis of said pipe structure;

connecting a plurality of said cut members to each other along said cutting edges to form a connected structure whereby said connected structure has an arc-shaped portion; and forming a second resin layer on an outer surface of said connected structure.

* * * * *